(12) United States Patent
Sato et al.

(10) Patent No.: US 8,774,340 B2
(45) Date of Patent: Jul. 8, 2014

(54) NUCLEAR REACTOR VIBRATION SURVEILLANCE SYSTEM AND ITS METHOD

(75) Inventors: Michio Sato, Kanagawa (JP); Mieko Sato, legal representative, Kanagawa (JP); Hidehiko Kuroda, Kanagawa (JP); Mikio Izumi, Kanagawa (JP); Mitsuhiro Enomoto, Kanagawa (JP); Masaki Yoda, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1346 days.

(21) Appl. No.: 12/409,151

(22) Filed: Mar. 23, 2009
(Under 37 CFR 1.47)

(65) Prior Publication Data

US 2009/0282920 A1 Nov. 19, 2009

(30) Foreign Application Priority Data

Mar. 25, 2008 (JP) .................. 2008-077296

(51) Int. Cl.
*G21C 17/003* (2006.01)
*G21C 17/00* (2006.01)

(52) U.S. Cl.
USPC ........................... 376/249; 376/245; 376/259

(58) Field of Classification Search
USPC ........ 376/245–253, 259, 463; 367/87, 88, 93, 367/94, 99, 117, 137, 138, 140, 141, 152; 342/21, 22, 59, 175, 192–197; 73/37, 73/570, 584, 596, 618, 620–633, 635, 637, 73/644, 700, 715, 716, 717, 722
See application file for complete search history.

(56) References Cited

U.S. PATENT DOCUMENTS

| | | | | | |
|---|---|---|---|---|---|
| 2,830,201 | A | * | 4/1958 | Wilson | 367/152 |
| 3,350,271 | A | * | 10/1967 | Maidment et al. | 376/252 |
| 3,545,262 | A | * | 12/1970 | Lockman et al. | 73/37 |
| 3,753,852 | A | * | 8/1973 | Scott et al. | 376/249 |
| 3,942,361 | A | * | 3/1976 | Rath et al. | 73/624 |
| 3,946,256 | A | * | 3/1976 | Day et al. | 73/632 |
| 3,988,922 | A | * | 11/1976 | Clark et al. | 367/117 |

(Continued)

FOREIGN PATENT DOCUMENTS

| | | |
|---|---|---|
| EP | 0 489 597 A2 | 6/1992 |
| JP | 5-040029 A | 2/1993 |

(Continued)

OTHER PUBLICATIONS

Machine translation of JP 11-125688 (Hashimoto et al.), Nov. 5, 1999.*

(Continued)

*Primary Examiner* — Bernarr Gregory
(74) *Attorney, Agent, or Firm* — Foley & Lardner LLP (57) ABSTRACT

A nuclear reactor vibration surveillance system has a first ultrasonic transducer for transmission, an ultrasonic transmitter, a second ultrasonic transducer for reception, an ultrasonic receiver, a signal processor, and a display unit. The first ultrasonic transducer for transmission is arranged on the outer surface of a reactor pressure vessel and is configured to convert a transmission signal into an ultrasonic pulse signal and allow the ultrasonic pulse to be transmitted to a reactor internal component. The second ultrasonic transducer for reception is arranged on the outer surface of the reactor pressure vessel and is configured to receive a reflected ultrasonic pulse reflected by the reactor internal component and convert the received reflected ultrasonic pulse into a reception signal.

5 Claims, 10 Drawing Sheets

(56) References Cited

U.S. PATENT DOCUMENTS

| | | | | |
|---|---|---|---|---|
| 4,010,636 A | * | 3/1977 | Clark et al. | 73/637 |
| 4,165,649 A | * | 8/1979 | Greer, Jr. | 73/644 |
| 4,722,225 A | * | 2/1988 | Hardy et al. | 73/622 |
| 5,015,995 A | * | 5/1991 | Holroyd | 340/621 |
| 5,214,616 A | * | 5/1993 | Terhune et al. | 367/99 |
| 5,319,683 A | * | 6/1994 | Kurek et al. | 376/245 |
| 5,327,783 A | * | 7/1994 | Au-Yang | 367/99 |
| 5,377,237 A | * | 12/1994 | Richardson et al. | 376/252 |
| 6,016,701 A | | 1/2000 | McClelland et al. | 73/620 |
| 6,957,583 B2 | * | 10/2005 | Tooma et al. | 73/625 |
| 7,735,373 B2 | * | 6/2010 | Cho et al. | 73/722 |
| 7,894,306 B2 | * | 2/2011 | Bagshaw et al. | 367/137 |
| 2008/0037695 A1 | | 2/2008 | Kono et al. | |

FOREIGN PATENT DOCUMENTS

| | | |
|---|---|---|
| JP | 7-151894 A | 6/1995 |
| JP | 09-243608 A | 9/1997 |
| JP | 11-125688 A | 5/1999 |
| JP | 2003-028841 A | 1/2003 |
| JP | 2004-020540 A | 1/2004 |
| JP | 2004-170399 A | 6/2004 |
| JP | 2005-127870 A | 5/2005 |
| JP | 2007-067500 A | 3/2007 |
| JP | 2007-121067 A | 5/2007 |
| JP | 2008-039622 A | 2/2008 |

OTHER PUBLICATIONS

Handbook of Ultrasonic Technology, Nikkan Kogyo Shinbun Ltd., revised fourth edition, pp. 1202-1203.

Handbook of Non-destructive Inspection [new edition], edited by the Japanese Society for Non-Destructive Inspection, Apr. 1978, pp. 458 to 459).

Handbook of New Non-destructive Inspection, edited by the Japanese Society for Non-Destructive Inspection, Oct. 1992, pp. 313 to 314.

* cited by examiner

NUCLEAR REACTOR VIBRATION SURVEILLANCE SYSTEM AND ITS METHOD

CROSS REFERENCES TO RELATED APPLICATIONS

This application is based upon and claims the benefits of priority from the prior Japanese Patent Applications No. 2008-077296, filed in the Japanese Patent Office on Mar. 25, 2008, the entire content of which is incorporated herein by reference.

BACKGROUND OF THE INVENTION

The present invention relates to a nuclear reactor vibration surveillance system for structural integrity monitoring of a nuclear reactor internal component and its method.

As a technique for checking the structural health of a nuclear reactor internal component, there is known a method that measures the vibration amplitude or vibration frequency of the reactor internal component and evaluates the measurement values or trend thereof. In order to measure the vibration of the reactor internal component, a method is generally adopted in which a vibration sensor is installed in the reactor, and a signal from the vibration sensor is sent outside the reactor by means of a signal cable.

However, in this method, it is necessary to lay the signal cable inside and outside the nuclear reactor, so that it takes quite a lot of work to prepare for the measurement.

In order to cope with this problem, an ultrasonic vibration measurement system has been proposed as disclosed in Japanese Patent No. 3,782,559 (the entire content of which is incorporated herein by reference).

In this ultrasonic vibration measurement system, an ultrasonic sensor is placed on the outer surface of a reactor pressure vessel, and an ultrasonic pulse is allowed to propagate in the reactor through the reactor pressure vessel. The ultrasonic pulse propagating in the reactor collides with and reflected by a reactor internal component such as a shroud or jet pump under water. The reflected ultrasonic pulse is retuned once again to the ultrasonic sensor through the reactor pressure vessel.

If the reactor internal component such as a shroud vibrates, the propagation time of the returned reflected ultrasonic pulse is slightly changed due to the vibration. Assuming that the change in the propagation time of the ultrasonic pulse is $\Delta t$ (sec), the vibration amplitude L (m) of the reactor internal component such as a shroud is calculated by using the following equation (1).

$$\Delta L = \frac{C\Delta t}{2} \quad (1)$$

"C" is the acoustic velocity (m/sec) of reactor water.

By plotting the $\Delta L$ in time series, the vibration waveform of the reactor internal component such as a shroud can be synthesized.

In the conventional nuclear reactor vibration surveillance system and its method, an ultrasonic sensor employed is configured both as a transmitter and receiver of the ultrasonic. Thus, for example, in the case where the reactor internal component such as a jet pump is arranged inclined relative to the reactor pressure vessel, the ultrasonic pulse is obliquely reflected by the jet pump, so that the reflected ultrasonic pulse is not returned to the ultrasonic source position. As a result, the ultrasonic sensor cannot receive the reflected ultrasonic pulse, making it impossible to measure the vibration of the reactor internal component.

The present invention has been made to solve the above problem, and an object thereof is to provide a nuclear reactor vibration surveillance system for structural integrity monitoring of a nuclear reactor internal component and its method capable of measuring the vibration of an in-reactor stricture arranged inclined relative to a reactor pressure vessel.

BRIEF SUMMARY OF THE INVENTION

According to a first aspect of the present invention, there is provided a nuclear reactor vibration surveillance system comprising: a first ultrasonic transducer for transmission which is arranged on the outer surface of a reactor pressure vessel and is configured to convert a transmission signal into an ultrasonic pulse signal and allow the ultrasonic pulse to be transmitted to a reactor internal component; an ultrasonic transmitter which is electrically connected to the first ultrasonic transducer and is configured to transmit the transmission signal; a second ultrasonic transducer for reception which is arranged on the outer surface of the reactor pressure vessel and is configured to receive a reflected ultrasonic pulse reflected by the reactor internal component and convert the received reflected ultrasonic pulse into a reception signal; an ultrasonic receiver which is electrically connected to the second ultrasonic transducer and is configured to receive the reception signal; a signal processor which is electrically connected to the ultrasonic transmitter and ultrasonic receiver and is configured to input a signal to the ultrasonic transmitter and receive a signal from the ultrasonic receiver so as to apply signal processing to the signal; and a display unit which is configured to display vibration information of the reactor internal component obtained as a result of the signal processing by the signal processor.

According to a second aspect of the present invention, there is provided a nuclear reactor vibration surveillance method comprising: allowing an ultrasonic pulse to be transmitted to a reactor internal component using a first ultrasonic transducer for transmission which is arranged on the outer surface of a reactor pressure vessel; receiving a reflected ultrasonic pulse reflected by the reactor internal component using a second ultrasonic transducer for reception which is arranged on the outer surface of the reactor pressure vessel; and applying signal processing to the received reflected ultrasonic pulse signal to measure the vibration of the reactor internal component.

BRIEF DESCRIPTION OF THE DRAWINGS

The above and other features and advantages of the present invention will become apparent from the discussion hereinbelow of specific, illustrative embodiments thereof presented in conjunction with the accompanying drawings, in which:

FIGS. 4A to 4C are explanatory views showing the ultrasonic pulse to be transmitted of FIG. 1 and ultrasonic pulses to be received of FIG. 1, in which

FIGS. 7A and 7B are explanatory views showing a time relationship and frequency relationship between a transmission RF pulse and a reception RF pulse of FIG. 6, in which

FIGS. 8A and 8B are explanatory views showing a configuration of a nuclear reactor vibration surveillance system according to a third embodiment of the present invention, in which

FIGS. 9A and 9B are explanatory views showing a configuration of a nuclear reactor vibration surveillance system according to a fourth embodiment of the present invention, in which

FIGS. 10A and 10B are explanatory views showing a configuration of a nuclear reactor vibration surveillance system according to a fifth embodiment of the present invention, in which

FIGS. 11A and 11B are explanatory views showing a configuration of a nuclear reactor vibration surveillance system according to a sixth embodiment of the present invention, in which FIGS. 12A and 12B are explanatory views showing a configuration of a nuclear reactor vibration surveillance system according to a seventh embodiment of the present invention, in which

DETAILED DESCRIPTION OF THE INVENTION

Embodiments of a nuclear reactor vibration surveillance system and its method will be described below with reference to the accompanying drawings, in which the same numerals are given to the same components and thus the overlapped descriptions will be omitted.

First Embodiment

Figure 1:
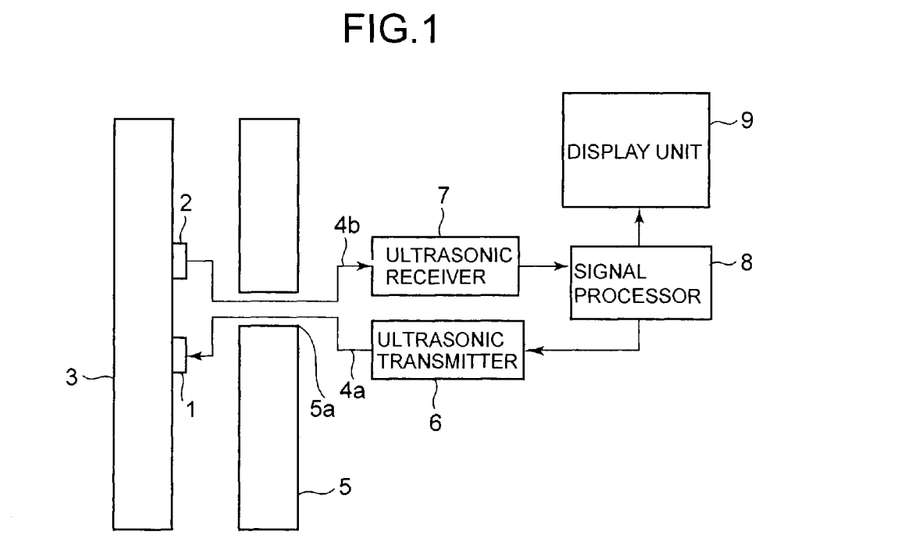
FIG. 1 is a view schematically showing a configuration of a nuclear reactor vibration surveillance system according to a first embodiment of the present invention.

FIG. 1 is a view schematically showing a configuration of a nuclear reactor vibration surveillance system according to a first embodiment of the present invention.

A basic configuration of the nuclear reactor vibration surveillance system will be described with reference to FIG. 1.

As shown in FIG. 1, an ultrasonic transducer 1 for transmission and an ultrasonic transducer 2 for reception are arranged on the outer surface of a reactor pressure vessel 3. The ultrasonic transducer 1 for transmission is electrically connected to an ultrasonic transmitter 6 arranged outside or inside a containment vessel 5 through a cable 4a by way of a containment vessel signal outlet port 5a of the containment vessel 5.

Similarly, the ultrasonic transducer 2 for reception is electrically connected to an ultrasonic receiver 7 arranged outside or inside a containment vessel 5 through a cable 4b by way of a containment vessel signal outlet port 5a of the containment vessel 5.

The ultrasonic transmitter 6 and the ultrasonic receiver 7 are electrically connected to a signal processor 8. The signal processor 8 is electrically connected to a display unit 9. The display unit 9 is configured to display a vibration waveform, vibration spectrum or the like analyzed by the signal processor 8.

Figure 2:
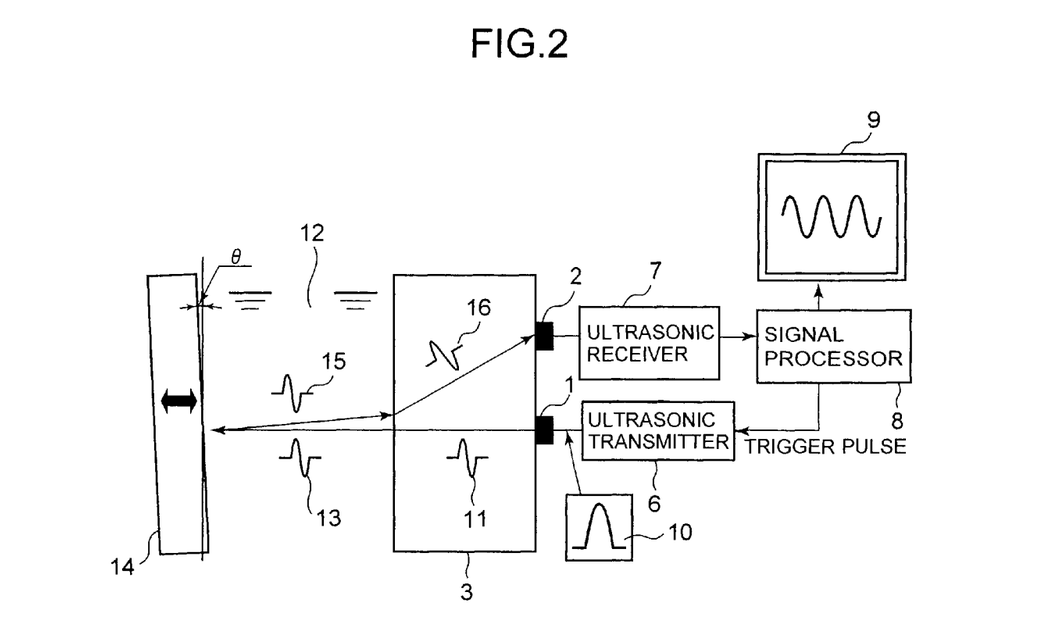
FIG. 2 is an explanatory view showing a propagation state of an ultrasonic signal of FIG. 1.

FIG. 2 is an explanatory view showing a propagation state of an ultrasonic signal of FIG. 1.

As shown in FIG. 2, a trigger pulse is input from the signal processor 8 to the ultrasonic transmitter 6 disposed at the outer surface of the reactor pressure vessel 3. When an electrical pulse signal 10 is added to the ultrasonic transducer 1 for transmission by the ultrasonic transmitter 6, the electrical pulse signal 10 is converted into an ultrasonic signal in the ultrasonic transducer 1 for transmission and, accordingly, an ultrasonic pulse 11 is generated.

The generated ultrasonic pulse 11 propagates into the reactor water 12 through the wall of the reactor pressure vessel 3. An incident ultrasonic pulse 13 that has propagated in the reactor water 12 is reflected by a reactor internal component 14 such as a jet pump. When the surface of the reactor internal component 14 is inclined relative to the reactor pressure vessel 3, a reflected ultrasonic pulse 15 propagates in an inclined direction corresponding to the inclination angle of the reactor internal component 14 according to the law of reflection.

The reflected ultrasonic pulse 15 propagates at an inclination angle until it reaches the boundary between the reactor water 12 and the reactor pressure vessel 3. At this time, the reflected ultrasonic pulse 15 becomes a reflected ultrasonic pulse 16 which propagates in the reactor pressure vessel 3 at a larger inclination angle due to refraction.

The ultrasonic transducer 2 for reception, which is arranged at a reaching point of the reflected ultrasonic pulse 16 that has previously calculated, detects the reflected ultrasonic pulse 16. The reflected ultrasonic pulse 16 detected in this manner is converted into an electrical pulse signal in the ultrasonic transducer 2 for reception. The electrical pulse signal is then subjected to signal processing such as amplification, filtering and the like in the ultrasonic receiver 7.

The signal processed in the ultrasonic receiver 7 is converted into a digital signal by the signal processor 8 which is constituted by a microcomputer or a frequency demodulator (FM demodulator, FM: Frequency Modulation), whereby vibration information is obtained.

Then, the vibration information of the reactor internal component 14 obtained through the processing in the signal processor 8 is displayed on the display unit 9. More specifically, the display unit 9 displays the input information including a vibration amplitude waveform, vibration frequency response, change trend of a vibration amplitude or vibration phase.

In the present embodiment described above, a method of measuring the vibration using an ultrasonic pulse signal will be described with reference to FIG. 3.

Figure 3:
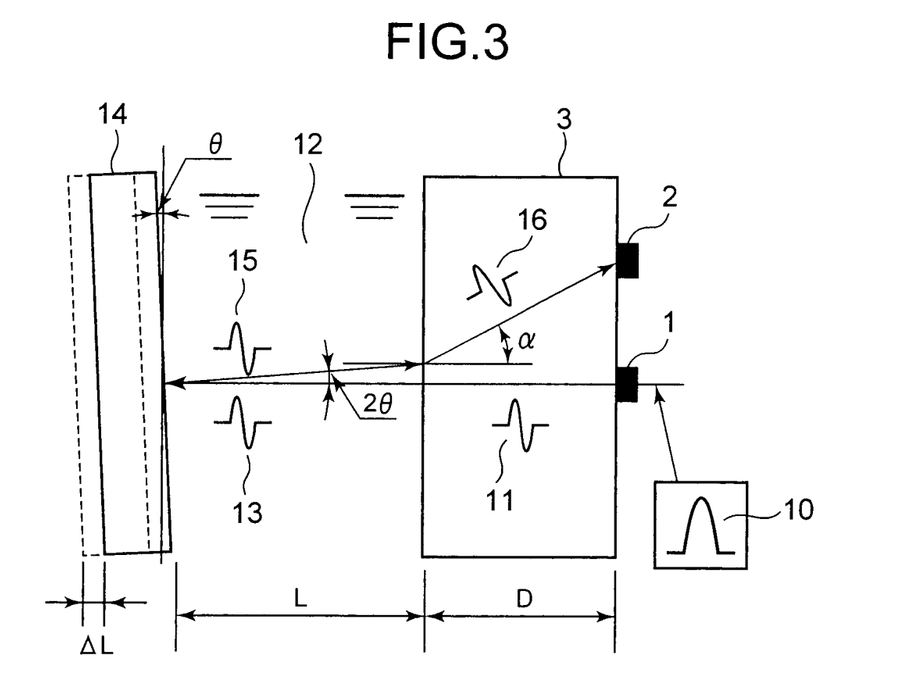
FIG. 3 is an explanatory view showing a method of measuring the vibration using the reflected ultrasonic signal of FIG. 1.

FIG. 3 is an explanatory view showing a method of measuring the vibration using the reflected ultrasonic signal of FIG. 1.

As shown in FIG. 3, a DC (Direct Current) pulse signal is used as the electric pulse signal 10 to be converted into an ultrasonic pulse. The ultrasonic pulse 11 from the ultrasonic transducer 1 for transmission is transmitted through the reactor pressure vessel 3 at a right angle relative to a wall of the reactor pressure vessel 3. In the reactor water 12, the incident ultrasonic pulse 13 propagates at a right angle relative to a wall of the reactor pressure vessel 3. The incident ultrasonic pulse 13 is reflected by the reactor internal component 14.

When the reactor internal component 14 is inclined at an angle of θ (degrees) relative to the reactor pressure vessel 3, the reflected ultrasonic pulse 15 propagates in the direction of 2θ (degrees). At the time when the reflected ultrasonic pulse 15 reaches the boundary between the reactor water 12 and the reactor pressure vessel 3, the ultrasonic pulse 16 is further refracted due to oblique propagation of the ultrasonic pulse because of a difference in the acoustic velocity between the reactor water 12 and the reactor pressure vessel 3.

That is, the refraction angle α (degrees) at which the reflected ultrasonic pulse 15 propagates in the reactor pressure vessel 3 is calculated by using the following equation (2) according to Snell's law.

$$\alpha = \sin^{-1}\left(\frac{C_{vessel}}{C_{water}}\sin 2\theta\right) \quad (2)$$

In the above equation, "Cwater" is the acoustic velocity (m/sec) of an ultrasonic wave in the reactor water 12, and "Cvessel" is the acoustic velocity (m/sec) of an ultrasonic wave in the reactor pressure vessel 3.

As is understood from the equation (2), the refraction angle α (degrees) is determined by the acoustic velocity of the reactor water. The acoustic velocity of the reactor water depends on the temperature of the reactor water.

As described above, the ultrasonic pulse that has propagated in the reactor pressure vessel 3 at the refraction angle α (degrees) is received by the ultrasonic transducer 2 for reception. In order to receive an ultrasonic echo with high sensitivity, the position of the ultrasonic transducer 2 for reception may need to be adjusted depending on the temperature of the reactor water. As described in Handbook of Ultrasonic Technology (Nikkan Kogyo Shinbun Ltd., revised fourth edition, pages 1,202 to 1,203), the acoustic velocity (Cwater) at a temperature of 25 degrees Celsius is 1,497 (m/sec), while the acoustic velocity (Cwater) at 287.8 degrees Celsius is reduced to 980 (m/sec). Assuming that the acoustic velocity (Cvessel) in the pressure vessel is 6,000 (m/sec) and θ is 1 degree, 8 degrees is obtained as the propagation angle α (25) at a temperature of 25 degrees Celsius, and 12.3 degrees is obtained as the propagation angle α (287.8) at 287.8 degrees Celsius. Here, it is assumed that the plate thickness of the nuclear reactor pressure vessel 3 is 160 mm. In this case, when the temperature of the reactor water is increased from 25 degrees Celsius to 287.8 degrees Celsius, the optimum reception position of the ultrasonic transducer 2 for reception is changed by about 12 mm (160 mm×tan(8 degrees)−160 mm×tan(12.3 degrees)=−12.4 mm).

As described in Handbook of Non-destructive Inspection [new edition] (edited by The Japanese Society for Non-Destructive Inspection, April, 1978, pages 458 to 459) and Handbook of New Non-destructive Inspection (edited by The Japanese Society for Non-Destructive Inspection, October, 1992, pages 313-314), an ultrasonic inspection method that uses two ultrasonic transducers to measure the plate thickness or detect defects has widely been used. In the above documents, the positions of the two ultrasonic transducers are determined in consideration of only the plate thickness D of the reactor pressure vessel 3. However, in order to receive the ultrasonic echo from the reactor internal component 14 at an optimum position, the position of the ultrasonic transducer 2 for reception is adjusted in consideration of the temperature of the reactor water in the present embodiment.

The ultrasonic transducer 2 for reception detects ultrasonic pulses 17a and 17b with respect to the electrical pulse signal 10 which is the ultrasonic pulse transmitted from the ultrasonic transducer 1 for transmission.

Figure 4A:
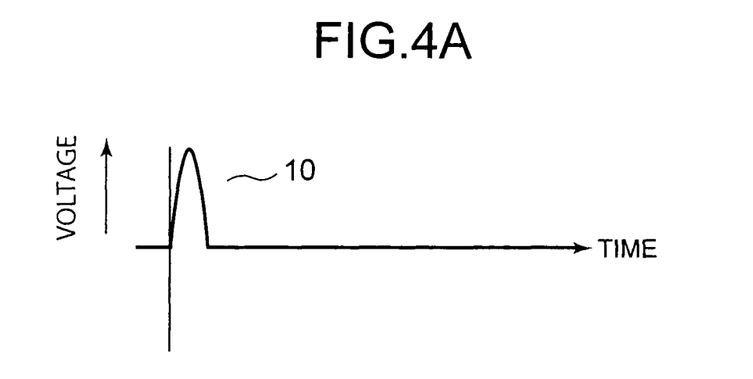
FIG. 4A is a timing chart of the electrical pulse signal which is the ultrasonic pulse transmitted from the ultrasonic transducer for transmission.
Figure 4B:
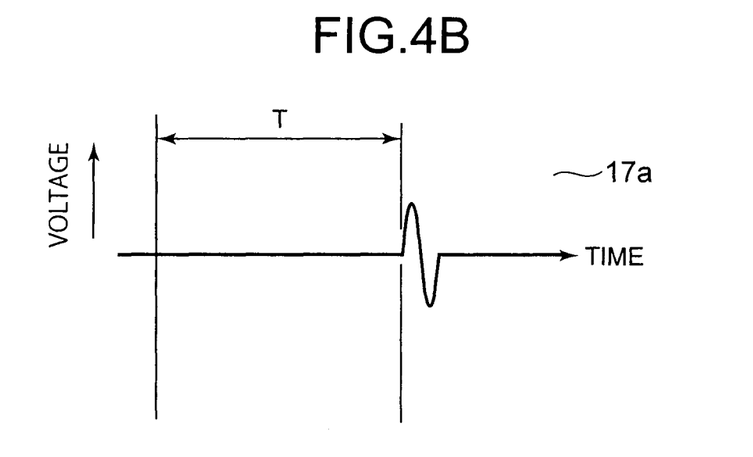
FIG. 4B is a timing chart of an ultrasonic pulse received by the ultrasonic transducer for reception.
Figure 4C:
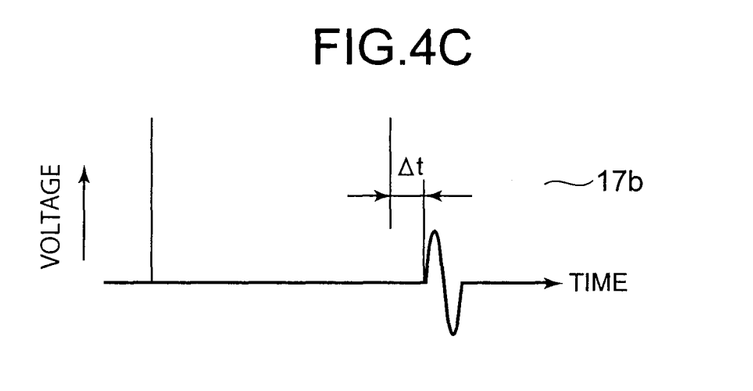
FIG. 4C is a timing chart of another ultrasonic pulse received by the ultrasonic transducer for reception.

FIGS. 4A to 4C are explanatory views showing the ultrasonic pulse to be transmitted of FIG. 1 and ultrasonic pulses to be received of FIG. 1. FIG. 4A is a timing chart of the electrical pulse signal 10 which is the ultrasonic pulse transmitted from the ultrasonic transducer 1 for transmission, FIG. 4B is a timing chart of the ultrasonic pulse 17a received by the ultrasonic transducer 2 for reception, and FIG. 4C is a timing chart of the ultrasonic pulse 17b received by the ultrasonic transducer 2 for reception.

When the reactor internal component 14 is vibrated, the arrival times at which the received ultrasonic pulse signals 17a and 17b are detected vary in proportion to the vibration amplitude of the reactor internal component. Assuming that the propagation time when the reactor internal component 14 is not vibrated is T (sec) as shown by a solid line in FIG. 3, the propagation time T is calculated using the following equation (3).

$$T = \frac{D}{C_{vessel}}\left(1 + \frac{1}{\cos\alpha}\right) + \frac{L}{C_{water}}\left(1 + \frac{1}{\cos 2\theta}\right) \quad (3)$$

Further, when the reactor internal component 14 is vibrated with a vibration amplitude of ΔL as shown by a broken line in FIG. 3, L becomes L+ΔL. Assuming that a change of the propagation time T of the ultrasonic pulse is Δt, the propagation time Δt is calculated by using the following equation (4).

$$\Delta t = \frac{D}{C_{vessel}}\left(1 + \frac{1}{\cos\alpha}\right) + \frac{L}{C_{water}}\left(1 + \frac{1}{\cos 2\theta}\right) - \\ \frac{D}{C_{vessel}}\left(1 + \frac{1}{\cos\alpha}\right) - \frac{L+\Delta L}{C_{water}} - \frac{L+\Delta L}{C_{water}}\left(1 + \frac{1}{\cos 2\theta}\right) \\ \Delta t = \frac{\Delta L}{C_{water}}\left(1 + \frac{1}{\cos 2\theta}\right) \quad (4)$$

Accordingly, the vibration amplitude ΔL is calculated by using the following equation (5).

$$\Delta L = C_{water}\frac{\cos 2\theta}{1+\cos 2\theta}\Delta t \quad (5)$$

Thus, by measuring the change Δt of the propagation time in the signal processor 8 shown in FIG. 1, the vibration amplitude ΔL can be measured.

Assuming that the time interval at which the ultrasonic pulse signal 10 is generated is Ts (sec), the vibration amplitude can discretely be measured for each time interval Ts (sec).

Figure 5:
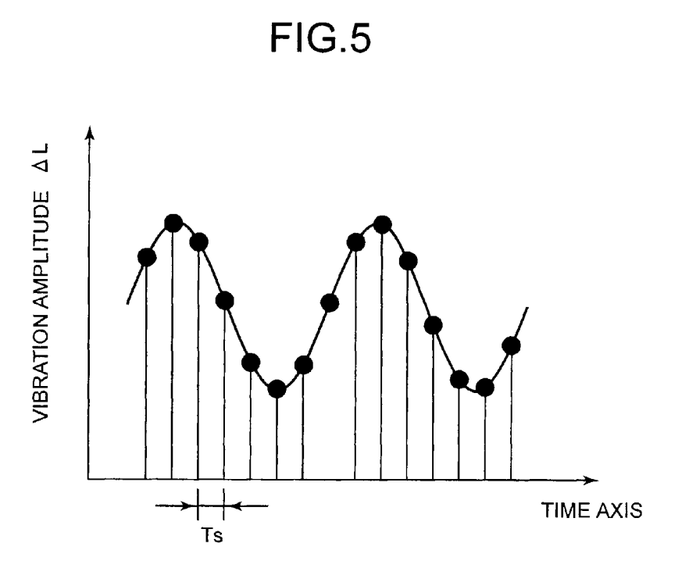
FIG. 5 is an explanatory view showing a method of reconstructing actual vibration amplitude from discrete measurement values of the vibration amplitude of FIG. 1.

FIG. 5 is an explanatory view showing a method of reconstructing actual vibration waveform from the discrete measurement values of the vibration amplitude of FIG. 1. As shown in FIG. 5, actual vibration waveform can be obtained.

The sampling theorem is used to reproduce a vibration signal having a frequency of f (Hz). The time interval Ts (sec) at which the ultrasonic pulse signal is generated, satisfy the following equation (6).

$$f \le \frac{1}{2Ts} \quad (6)$$

For example, in order to reproduce a vibration amplitude of 100 Hz, at least, the ultrasonic pulse signal should be generated at an interval of 200 Hz (Ts=50 msec).

According to the present embodiment, even when the reactor internal component 14 is arranged inclined relative to the reactor pressure vessel 3, the reflected ultrasonic pulses 17a and 17b from the reactor internal component 14 can be received by using the ultrasonic transducer 1 for transmission and ultrasonic transducer 2 for reception, whereby the vibration of the reactor internal component 14 can be measured.

Second Embodiment

Figure 6:
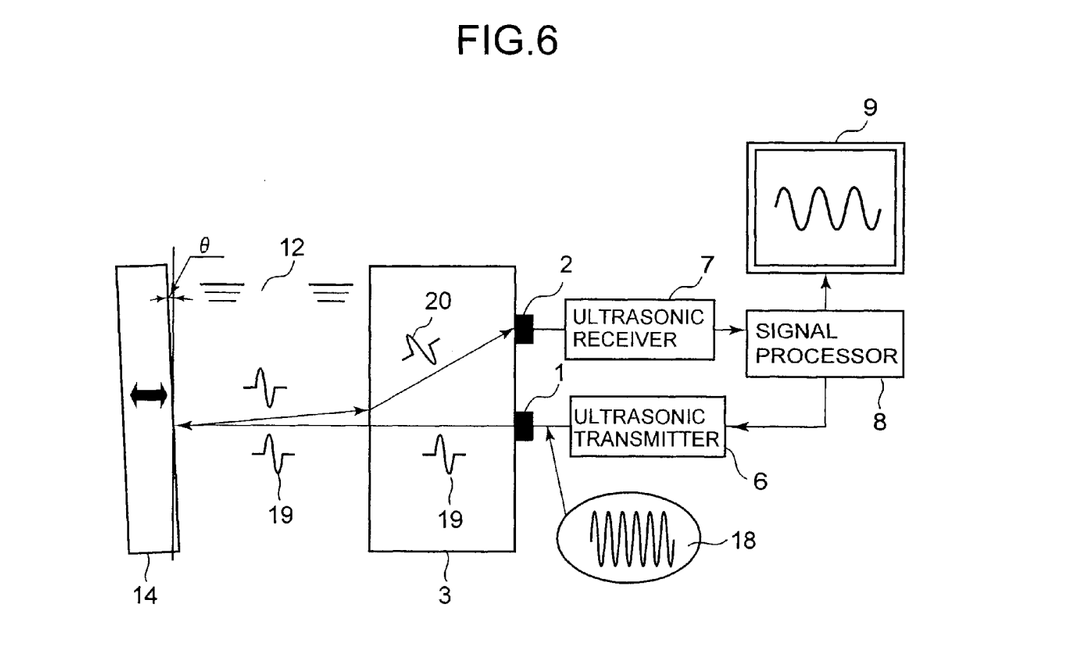
FIG. 6 is a view schematically showing a configuration of a nuclear reactor vibration surveillance system according to a second embodiment of the present invention.
Figure 7A:
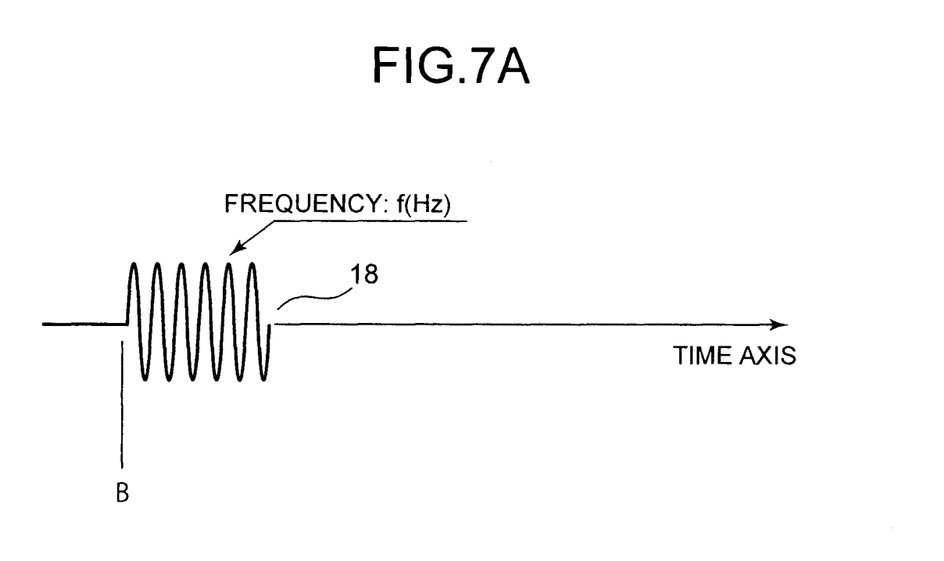
FIG. 7A is a timing chart of the transmission RF pulse transmitted from the ultrasonic transducer for transmission.
Figure 7B:
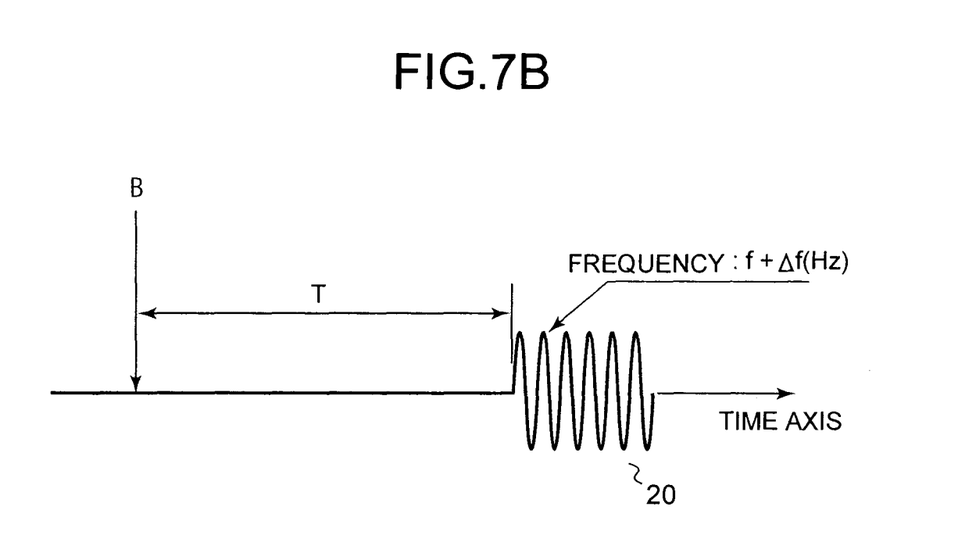
FIG. 7B is a timing chart of the reception RF pulse received by the ultrasonic transducer for reception.

FIG. 6 is a view schematically showing a configuration of a nuclear reactor vibration surveillance system according to a second embodiment of the present invention. FIGS. 7A and 7B are explanatory views showing a time relationship and frequency relationship between a transmission RF pulse and a reception RF pulse of FIG. 6. FIG. 7A is a timing chart of the transmission RF pulse transmitted from the ultrasonic transducer for transmission, and FIG. 7B is a timing chart of the reception RF pulse received by the ultrasonic transducer for reception. In FIG. 6, the same reference numerals as those in FIG. 1 denote the similar parts as those in FIG. 1, and thus the overlapped descriptions will be omitted.

As shown in FIG. 6 and FIG. 7A, an RF (Radio Frequency) pulse signal 18 is used as an ultrasonic pulse signal to be generated from the ultrasonic transmitter 6. That is, when the RF pulse signal 18 shown in FIG. 7A is input to the ultrasonic transducer 1 for transmission, an incident ultrasonic RF pulse 19 generated at that time also becomes an RF pulse signal. The frequency of the carrier of the RF pulse signal thus generated is assumed to be f (Hz). This RF pulse signal propagates in the reactor water 12, reflected by the reactor internal component 14, refracted at the boundary between the reactor water 12 and the reactor pressure vessel 3, and received by the ultrasonic transducer 2 for reception.

The received reception RF pulse signal 20 is observed at a time interval of the propagation time T or (T+Δt), as in the case of the ultrasonic pulse signal to be transmitted and ultrasonic pulse signal to be received of FIG. 4. The reflected RF pulse signal is Doppler-shifted by the vibration of the reactor internal component 14 and, accordingly, the frequency of the reflected RF pulse signal is changed.

Assuming that the vibration speed of the reactor internal component 14 is V (m/sec), the frequency change Δf (Hz) in this case can be calculated by using the following equation (7).

$$\Delta f = 2f \frac{V}{C_{water}} \cos 2\theta \quad (7)$$

In the above equation, "Cwater" is the acoustic velocity (m/sec) of an ultrasonic wave in the reactor water 12, and θ is the inclination angle (degrees) between the reactor pressure vessel 3 and the reactor internal component 14 shown in FIG. 6.

The frequency change Δf is measured in the signal processor 8 shown in FIG. 6 using a frequency demodulation circuit. The vibration speed V (m/sec) can be calculated back from the frequency change Δf obtained using the equation (7). Also in this case, the vibration speed is discretely measured and, therefore, as in the case of the method shown in FIG. 5, the measurement value is input to the signal processor 8 and then the sampling theorem is used to synthesize a vibration speed waveform. The obtained data is then converted into a vibration amplitude waveform or vibration acceleration waveform, which is then displayed on the display unit 9.

According to the present embodiment, by using the RF pulse signal 18 in place of the DC pulse signal used in the first embodiment, it is possible to detect the Doppler shift of the ultrasonic pulse signal generated with the vibration of the reactor internal component 14 to allow the vibration amplitude and vibration speed to be measured simultaneously, thereby improving measurement accuracy.

Third Embodiment

Figure 8A:
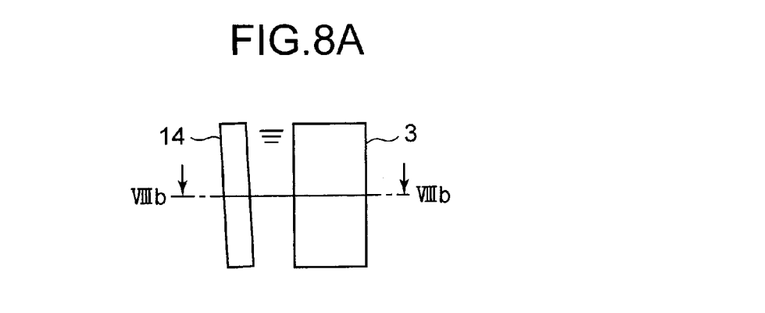
FIG. 8A is a view showing a positional relationship between the reactor pressure vessel and reactor internal component.
Figure 8B:
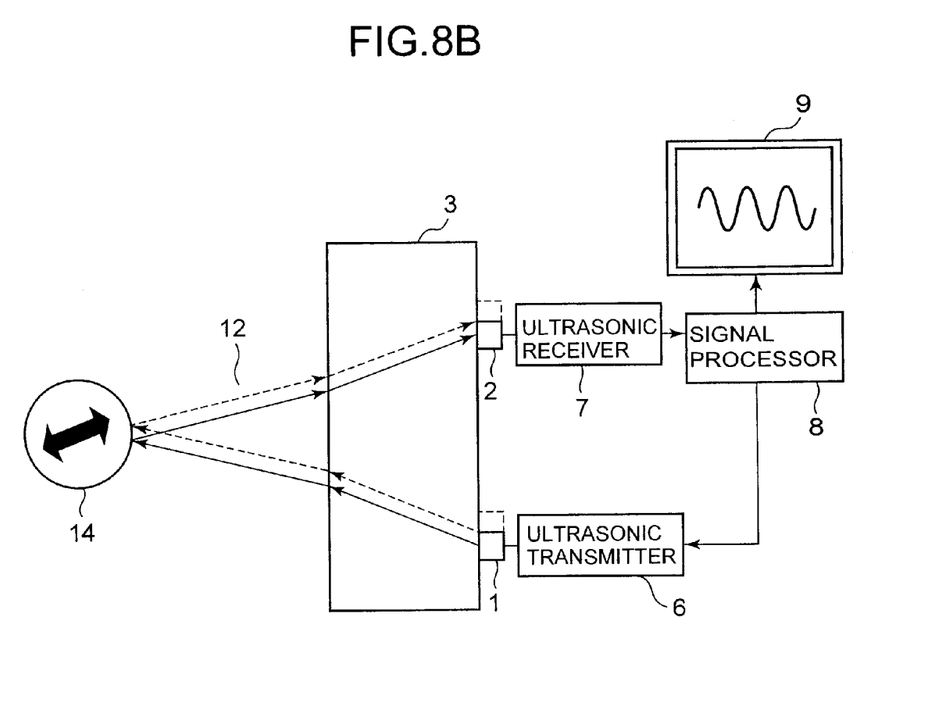
FIG. 8B is a cross-sectional view taken along VIIIb-VIIIb of FIG. 8A as viewed from above.

FIGS. 8A and 8B are explanatory views showing a configuration of a nuclear reactor vibration surveillance system according to a third embodiment of the present invention. FIG. 8A is a view showing a positional relationship between the reactor pressure vessel and reactor internal component, and FIG. 8B is a cross-sectional view taken along VIIIb-VIIIb of FIG. 8A as viewed from above. In FIGS. 8A and 8B, the same reference numerals as those in FIG. 1 denote the similar parts as those in FIG. 1, and thus the overlapped descriptions will be omitted.

As shown in FIG. 8B, the reactor internal component 14 is represented by a circle. The ultrasonic transducer 1 for transmission is moved on the outer surface of the reactor pressure vessel 3 in the circumferential direction so that the position at which the ultrasonic pulse reflects onto the reactor internal component 14 is changed. Correspondingly, the position of the ultrasonic transducer 2 for reception is moved.

According to the present embodiment, the vibration of the reactor internal component 14 can be measured even when the reactor internal component 14 has a curved surface. Further, by using the vibration waveforms before and after change of the vibration measurement position, the vibration of the reactor internal component 14 can be measured more in detail.

Fourth Embodiment

Figure 9A:
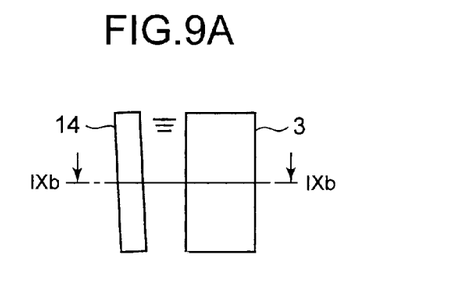
FIG. 9A is a view showing a positional relationship between the reactor pressure vessel and reactor internal component.
Figure 9B:
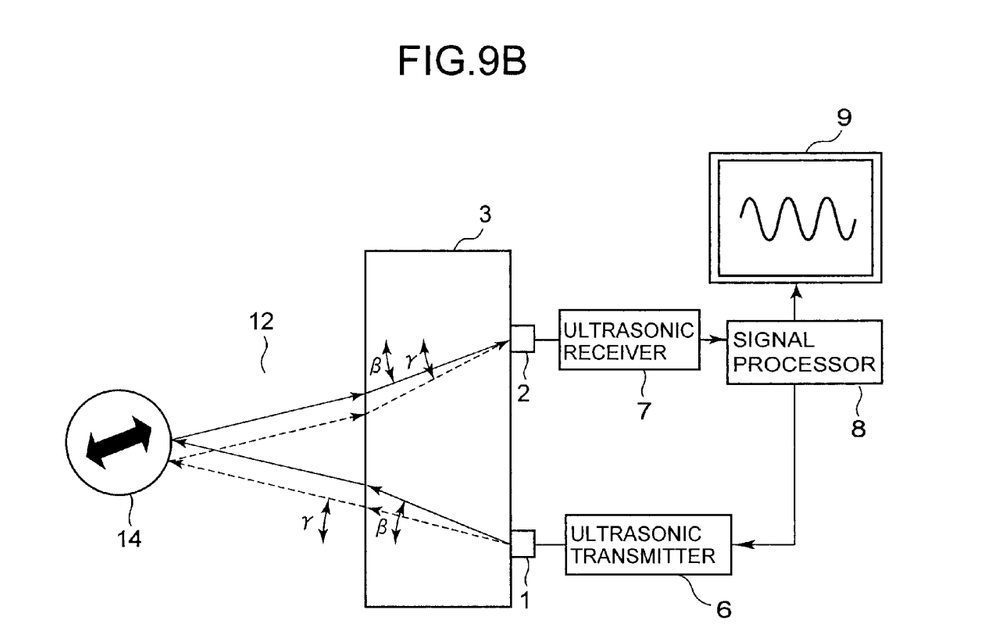
FIG. 9B is a cross-sectional view taken along IXb-IXb of FIG. 9A as viewed from above.

FIGS. 9A and 9B are explanatory views showing a configuration of a nuclear reactor vibration surveillance system according to a fourth embodiment of the present invention. FIG. 9A is a view showing a positional relationship between the reactor pressure vessel and reactor internal component, and FIG. 9B is a cross-sectional view taken along IXb-IXb of FIG. 9A as viewed from above.

As shown in FIG. 9B, the reactor internal component 14 is represented by a circle. The incident angle of the ultrasonic pulse to be transmitted from the ultrasonic transducer 1 for transmission is changed from β to γ so that position at which the ultrasonic pulse reflects onto the reactor internal component 14 is changed. Correspondingly, the reception angle of the ultrasonic pulse received by the ultrasonic transducer 2 for reception is changed from β to γ.

According to the present embodiment, by changing the ultrasonic pulse incident angle from β to γ, it is possible to change the measurement point of the vibration without moving the positions of the ultrasonic transducer 1 for transmission. Further, by using the vibration waveforms of the reactor internal component 14 before and after the change of the incident angle and reception angle, the vibration of the reactor internal component 14 can be measured more in detail.

Fifth Embodiment

Figure 10A:
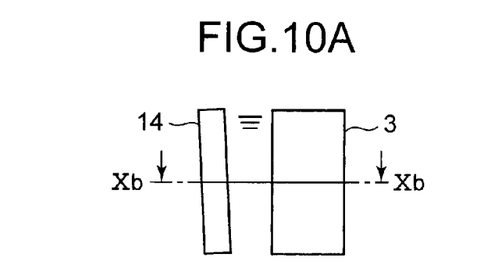
FIG. 10A is a view showing a positional relationship between the reactor pressure vessel and reactor internal component.
Figure 10B:
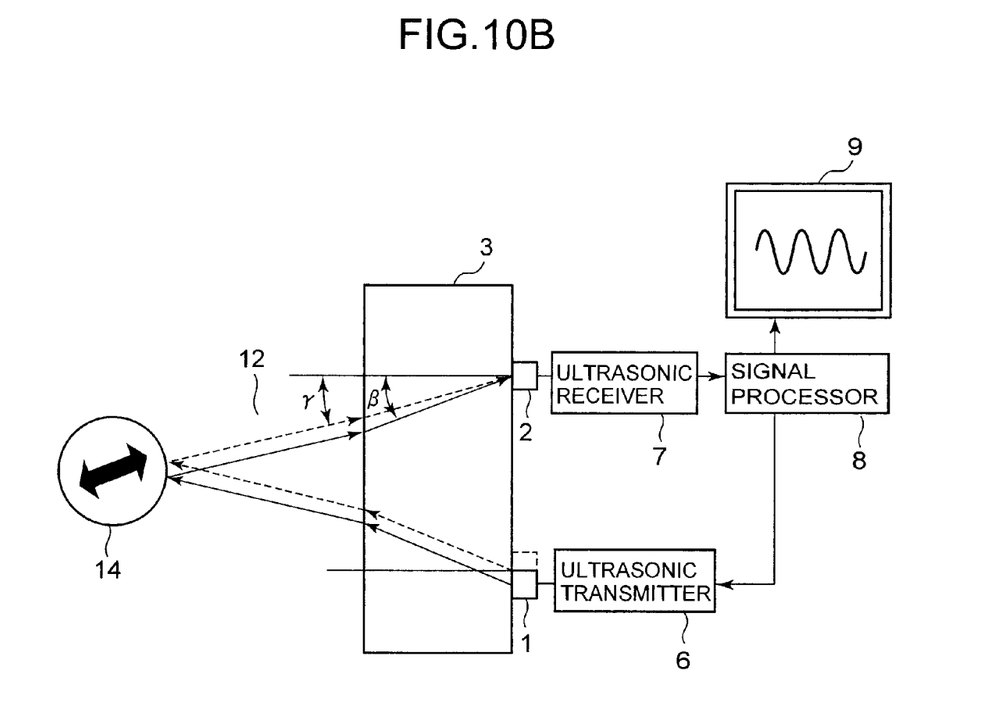
FIG. 10B is a cross-sectional view taken along Xb-Xb of FIG. 10A as viewed from above.

FIGS. 10A and 10B are explanatory views showing a configuration of a nuclear reactor vibration surveillance system according to a fifth embodiment of the present invention. FIG. 10A is a view showing a positional relationship between the reactor pressure vessel and reactor internal component, and FIG. 10B is a cross-sectional view taken along Xb-Xb of FIG. 10A as viewed from above. In FIGS. 10A and 10B, the same reference numerals as those in FIG. 1 denote the similar parts as those in FIG. 1, and thus the overlapped descriptions will be omitted.

As shown in FIG. 10B, the reactor internal component 14 is represented by a circle. The position of the ultrasonic transducer 1 for transmission is changed so that the position at which the ultrasonic pulse reflects onto the reactor internal component 14 is changed. Correspondingly, the reception angle of the ultrasonic pulse is changed from β to γ without moving the ultrasonic transducer 2 for reception.

According to the present embodiment, it is possible to change the measurement position of the vibration without moving the ultrasonic transducer 2 for reception. Further, by using the vibration waveforms of the reactor internal component 14 before and after the change of the position of the ultrasonic transducer 1 for transmission, the vibration of the reactor internal component 14 can be measured more in detail.

Sixth Embodiment

Figure 11A:
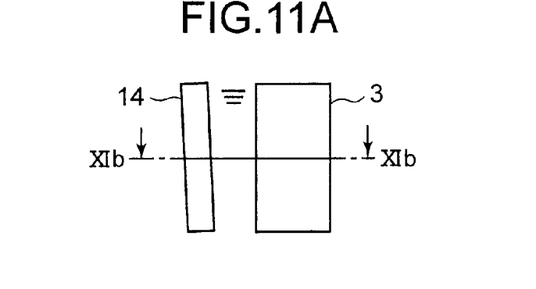
FIG. 11A is a view showing a positional relationship between the reactor pressure vessel and reactor internal component.
Figure 11B:
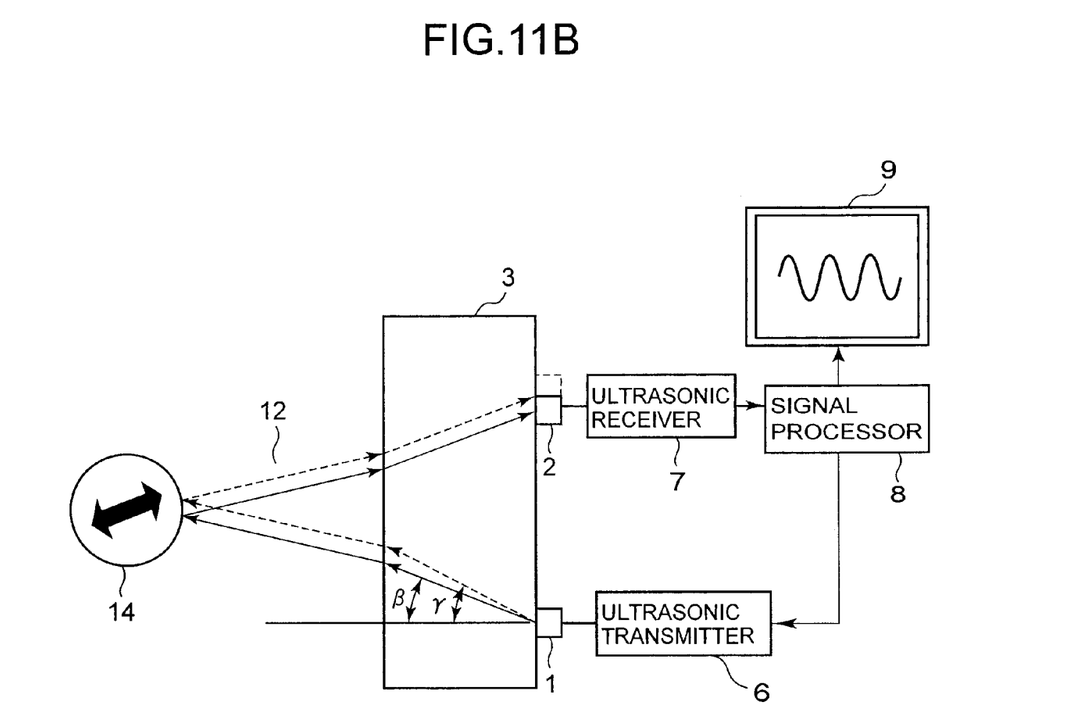
FIG. 11B is a cross-sectional view taken along XIb-XIb of FIG. 11A as viewed from above.

FIGS. 11A and 11B are explanatory views showing a configuration of a nuclear reactor vibration surveillance system according to a sixth embodiment of the present invention. FIG. 11A is a view showing a positional relationship between the reactor pressure vessel and reactor internal component, and FIG. 11B is a cross-sectional view taken along XIb-XIb of FIG. 11A as viewed from above. In FIGS. 11A and 11B, the same reference numerals as those in FIG. 1 denote the similar parts as those in FIG. 1, and thus the overlapped descriptions will be omitted.

As shown in FIG. 11B, the reactor internal component 14 is represented by a circle. The incident angle of the ultrasonic pulse to be transmitted from the ultrasonic transducer 1 for transmission is changed from β to γ without moving the ultrasonic pulse of the ultrasonic transducer 1 for transmission so that position at which the ultrasonic pulse reflects onto the reactor internal component 14 is changed. Correspondingly, the position of the ultrasonic transducer 2 for reception is moved to change the reception position of the ultrasonic pulse.

According to the present embodiment, it is possible to change the measurement position of the vibration without moving the ultrasonic transducer 1 for transmission. Further, by using the vibration waveforms of the reactor internal component 14 before and after the change of the position of the ultrasonic transducer 2 for reception, the vibration of the reactor internal component 14 can be measured more in detail.

Seventh Embodiment

Figure 12A:
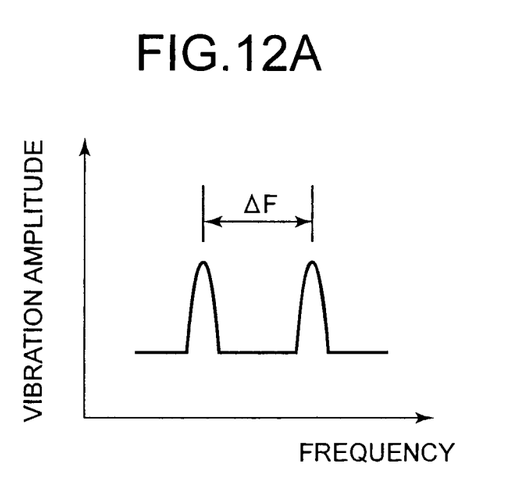
FIG. 12A is a characteristic view showing a display method of the original frequency of the reactor internal component 14.
Figure 12B:
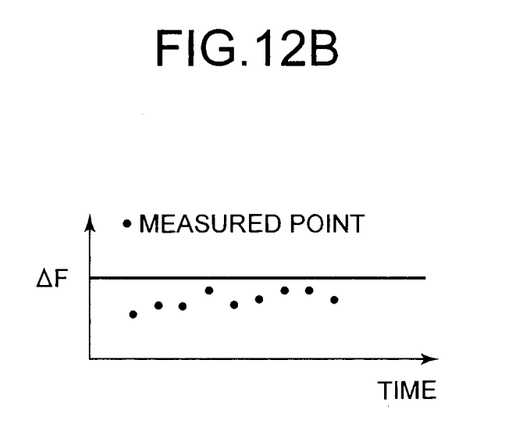
FIG. 12B is a characteristic view showing a setting method of a threshold value.

FIGS. 12A and 12B are explanatory views showing a configuration of a nuclear reactor vibration surveillance system according to a seventh embodiment of the present invention. FIG. 12A is a characteristic view showing a display method of the original frequency of the reactor internal component which have no extraordinary frequency, and FIG. 12B is a characteristic view showing a setting method of a threshold value.

As shown in FIG. 12A, the frequency analysis of the vibration information of the reactor internal component 14 which has been obtained through the processing of the signal processor 8 is performed to calculate the difference in frequency ΔF. Then, as shown in FIG. 12B, the temporal change of the difference in frequency ΔF of the reactor internal component 14 is displayed on the display unit 9.

According to the present embodiment, the temporal change of the difference in frequency ΔF is displayed based on the measured vibration signal. This makes it easier to grasp occurrence of abnormal vibration, thereby increasing reliability of the vibration surveillance.

Although the present invention has been described with reference to the preferred embodiments, the present invention is not limited to the above embodiments but may be modified in various ways by combining the configurations of the above embodiments without departing from the scope of the present invention.

What is claimed is:

1. A nuclear reactor vibration surveillance system comprising:
    a first ultrasonic transducer for transmission which is arranged on the outer surface of a reactor pressure vessel and is configured to convert a transmission signal into an ultrasonic pulse signal and allow the ultrasonic pulse to be transmitted to a reactor internal component;
    an ultrasonic transmitter which is electrically connected to the first ultrasonic transducer and is configured to transmit the transmission signal;
    a second ultrasonic transducer for reception which is arranged separately from the first ultrasonic transducer on the outer surface of the reactor pressure vessel and is configured to receive a reflected ultrasonic pulse, which is transmitted by the first ultrasonic transducer and reflected by the reactor internal component, and to convert the received reflected ultrasonic pulse into a reception signal;
    an ultrasonic receiver which is electrically connected to the second ultrasonic transducer and is configured to receive the reception signal;
    a signal processor which is electrically connected to the ultrasonic transmitter and ultrasonic receiver and is configured to input a signal to the ultrasonic transmitter and receive a signal from the ultrasonic receiver so as to apply signal processing to the signal; and
    a display unit which is configured to display vibration information of the reactor internal component obtained as a result of the signal processing by the signal processor.

2. The nuclear reactor vibration surveillance system according to claim 1, wherein the first ultrasonic transducer is configured to change the incident angle of the ultrasonic pulse.

3. The nuclear reactor vibration surveillance system according to claim 1, wherein the second ultrasonic transducer is configured to change the reception angle of the ultrasonic pulse.

4. The nuclear reactor vibration surveillance system according to claim 1, wherein the first ultrasonic transducer is configured to change the incident angle of the ultrasonic pulse, and the second ultrasonic transducer is configured to change the reception angle of the ultrasonic pulse.

5. The nuclear reactor vibration surveillance system according to claim 1, wherein the signal processor performs the frequency analysis for the received signal to calculate the original frequency of the reactor internal component which have no extraordinary frequency, and the display unit displays the temporal change of the difference in frequency.

* * * * *